(12) United States Patent
Happel

(10) Patent No.: US 7,102,133 B2
(45) Date of Patent: Sep. 5, 2006

(54) METHOD AND DEVICE FOR MEASURING A MASS FLOW

(75) Inventor: Jens Happel, Lübeck-Brandenburg (DE)

(73) Assignee: mic measuring ideas consulting GmbH, Emmendingen (DE)

( * ) Notice: Subject to any disclaimer, the term of this patent is extended or adjusted under 35 U.S.C. 154(b) by 319 days.

(21) Appl. No.: 10/484,954

(22) PCT Filed: Jul. 25, 2002

(86) PCT No.: PCT/EP02/08303

§ 371 (c)(1),
(2), (4) Date: Jan. 27, 2004

(87) PCT Pub. No.: WO03/012375

PCT Pub. Date: Feb. 13, 2003

(65) Prior Publication Data

US 2005/0001169 A1    Jan. 6, 2005

(30) Foreign Application Priority Data

Jul. 28, 2001  (DE)  ................................ 101 37 009

(51) Int. Cl.
*G01F 1/00* (2006.01)
(52) U.S. Cl. ...................... 250/356.1; 702/49
(58) Field of Classification Search ............ 250/356.1; 378/51; 702/49
See application file for complete search history.

(56) References Cited

U.S. PATENT DOCUMENTS

| | | | |
|---|---|---|---|
| 4,423,623 A | 1/1984 | Ho et al. | |
| 4,580,441 A | 4/1986 | Sakurai et al. | |
| 5,101,163 A | 3/1992 | Agar | |
| 5,177,444 A | 1/1993 | Cutmore | |
| 5,550,537 A | 8/1996 | Perdue | |
| 5,864,239 A | 1/1999 | Adams et al. | |
| 6,025,814 A | 2/2000 | Nelson et al. | |
| 6,037,783 A * | 3/2000 | Reich | ......... 324/639 |
| 6,109,097 A | 8/2000 | Conrads et al. | |
| 6,177,983 B1 | 1/2001 | Trainer | |
| 2002/0024666 A1* | 2/2002 | Thomasson et al. | ........ 356/342 |

FOREIGN PATENT DOCUMENTS

| | | |
|---|---|---|
| DE | 44 26 280 A1 | 2/1996 |
| EP | 0 717 269 A2 | 6/1996 |
| JP | 59019814 | 2/1998 |
| WO | 98/17978 | 4/1998 |

* cited by examiner

*Primary Examiner*—David Porta
*Assistant Examiner*—Djura Malevic
(74) *Attorney, Agent, or Firm*—Volpe and Koenig, P.

(57) ABSTRACT

A device used to measure the mass flow of a particulate transported with the aid of a gas. The device includes an arrangement which is used to create an electromagnetic field, with a measuring area being defined therein. An evaluation device for electromagnetic radiation which is reflected at least off of the solid(s) is connected to a detector. The evaluation device is provided with a differentiator which is connected to the detector for detecting reflected electromagnetic radiation. A rectifier is connected to the differentiator in order to determine an amount, whereby mass flow is obtained from the reflection amount. The reflection is measured, at least from the solid(s) within the measuring area of the magnetic field, whereupon the differential quotient is determined as a function of time from the chronological progression of the measuring signal and the absolute value is obtained therefrom. A measuring signal is obtained from the non-homogeneity of the electromagnetic field, forming the integral over time of the amount of the reflected power per time. The measuring signal is proportional to the mass flow.

21 Claims, 8 Drawing Sheets

At speed V = V1

At Speed V = V2 = 2 x V1

Fkt. P(t)=   a * t    P0    -a * t + P1

Fkt. P(t)= a * t        P0        -a * t + P1

At speed V = V2 = 2 x V1

Fkt. P(t)=2a * t  P0   -2a x t + P1

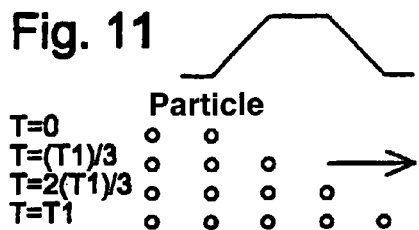
Fig. 11
T=0
T=(T1)/3
T=2(T1)/3
T=T1
Particle
Speed = V1
Conc. = C1
Reflected Power = P(t)
Time = t
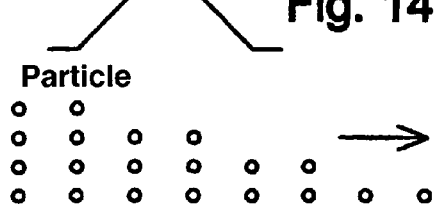
Fig. 14
Particle
Speed = V2=2xV1
Conc. = C2 = C1
Reflected Power = P(t)
Time = t
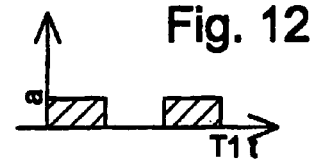
Fig. 12
At t = 0, particle enters the field,
At t = T1, particle leaves the field
Fig. 15
At t = 0, particle enters the field
At t = (T1)/2, particle leaves the field
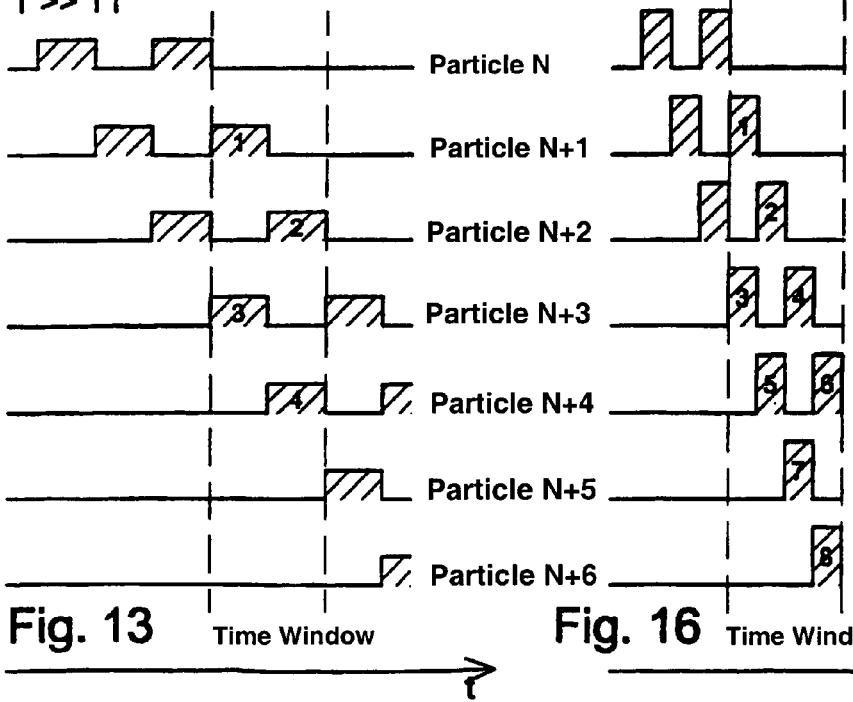
Fig. 13  Time Window
Fig. 16  Time Window

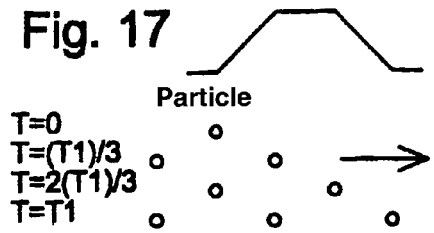
Fig. 17
Particle
T=0
T=(T1)/3
T=2(T1)/3
T=T1
Speed = V1
Conc. = C1
Reflected Power = P(t)
Time = t
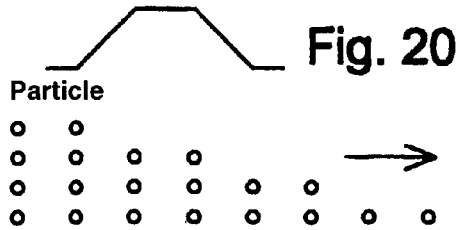
Fig. 20
Particle
Speed = V2=V1
Conc. = C2 = 2xC1
Reflected Power = P(t)
Time = t
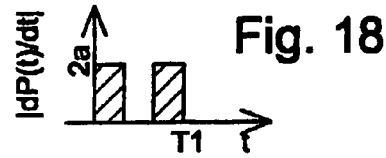
Fig. 18
At t = 0, particle enters field
At t = T1, particle leaves field
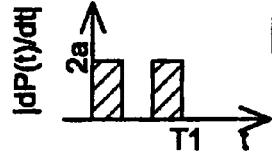
Fig. 21
At t = 0, particle enters field
At t = T1, particle leaves field
T >> T1
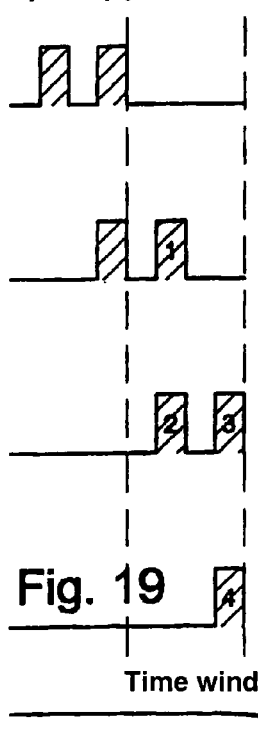
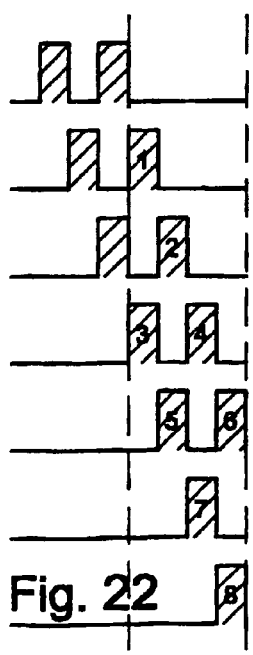
Particle N
Particle N+1
Particle N+2
Fig. 19
Particle N+3
Fig. 22
Time window    t
Time window    t

METHOD AND DEVICE FOR MEASURING A MASS FLOW

BACKGROUND

The invention relates to a method for measuring the mass flow of a particulate solid which is transported by means of a gas, a measuring region being defined in an electromagnetic field, and the electromagnetic radiation reflected by the solid(s) being evaluated. Moreover the invention relates to an arrangement for performing the method, which has a device for producing an electromagnetic field in which a measuring region is defined, and with an evaluation device, connected to a detector, for at least the electromagnetic radiation reflected from the solid(s).

A series of different methods and devices are known for the determination of the mass flow (also termed "throughput") of a solid which preferably passed through a tube with a transport gas, for example, air.

"Mass flow" will always be understood hereinafter the transport of a weight unit of a material in a given time unit: for example, Kg/s or t/h.

The solid is preferably comminuted or milled, so that as a rule it is present as a powder or dust. It can also, however, naturally have a granular appearance, such as is the case of cereals. As the electromagnetic waves, microwaves, visible light, or infrared can be used.

In all the measurement methods known heretofore, which use electromagnetic waves for mass flow determination, on the one hand the concentration, and in addition the speed, of the solid are measured. For concentration measurements the damping of the amplitude of an electromagnetic wave is frequently determined; for speed measurements, the frequency shift due to the Doppler effect is frequently used. Both measurement results are then multiplied together to give the mass flow. These mass flow measuring devices thus consist in principle of two measuring devices.

Methods and devices which operate according to this principle are known from, for example, WO90/03668, Patent Abstracts of Japan, Vol. 8, No. 109 (P-275), 22 May 1984, JP-A-59 019814, and U.S. Pat. No. 4,580,441.

From U.S. Pat. No. 5,550,537, it is known to determine the concentration of the transported solid using the reflected energy or power. The flow speed measurement takes place by measurement of the frequency shift of the reflected radiation due to the Doppler effect.

Here also, two measurements and two mutually separated evaluations are necessary. A corresponding cost for the measuring and evaluation devices, and also a doubled possibility of error, are present.

SUMMARY

The object of the present invention is to provide a method and a device of the kind mentioned at the beginning, making possible a simplified substantially error-free measurement, with simultaneously reduced expense.

To attain this object, it is proposed according to the method that the mass flow is determined from only the measure of reflection, that for this purpose the reflection is measured at least on the solid within the measuring region of the electromagnetic field, that from the time course of the measurement signal, the differential quotient according to time, or a derivative of higher order, and the absolute value thereof is determined. This signal available after sum formation is appropriately integrated for signal damping.

Through this measurement method, only a single measurement effect is evaluated, in order to determine the mass flow. Due to the inhomogeneity of the electromagnetic field, a measurement signal results which is the integral formed over time of the absolute value of the reflected power, derived over time. This measurement signal is proportional to the mass flow.

Expressed in a simplified manner, in this measurement method the particles are counted, since each particle produces the same signal independently of the concentration and speed at which it is forwarded. In addition, larger particles produce a larger signal than smaller particles of the same kind.

In the measurement method according to the invention, the total reflected radiation can be measured. This is sufficient because in an intermediate step in signal generation the derivative of the reflected power is formed, so that constant fractions of reflected power cancel out of the calculation. Thereby power reflected from pipe walls and/or adhered deposits does not lead to a false result.

Since the fraction of power reflected from pipe walls and/or deposits is often very much greater than that reflected from the solid, this can however lead to a poorer signal/noise ratio. In this case it is advantageous to measure only the radiation reflected from the solid, and for this purpose to measure the reflected radiation, frequency shifted due to the Doppler effect.

It is furthermore possible to use, instead of the reflected power, only the ratio or the difference of irradiated and reflected power, when the irradiated power is constant or known, or undergoes a known variation with time.

The device according to the invention for performing the method is in particular characterized in that the evaluation device has a differentiator connected to the detector for determining reflected, electromagnetic radiation, to which a rectifier is connected for absolute value formation. As already described in connection with the method according to the invention, the mass flow can then be determined, in that only a single measurement is evaluated. The cost of measurement technology is then correspondingly small, and the measurement device has a considerably reduced likelihood of error.

An intermediate stage for null point displacement is advantageously connected between the differentiator and the rectifier, and preferably has a capacitor for blocking direct currents. The null point, which does not lie in the center after the derivation, can thereby be correspondingly displaced, and the constant direct current fraction can be separated with the capacitor.

According to an embodiment of the invention, a portion of the signal preparation is provided by an analog circuit, and another portion of the signal preparation is provided by a digital circuit, in particular, an analog circuit for derivation with formation of differential quotients, and a digital circuit for sum formation and integration, are provided.

Furthermore, the possibility exists that the output of the rectifier, with the output signal originating there if necessary after smoothing with a capacitor, is connected to a digital function unit with an A/D converter and a processor.

Finally, a digital circuit can be provided for signal generation, the detector, if necessary after immediate matching, being directly connected to an A/D converter, and the latter to a processor. In the latter case, the processor first forms the derivative, then the sum of the derivatives, and finally performs the integration. The use of a digital processor has the advantage that it can also perform relatively simply the calibration or conversion of the signal into a suitable magnitude for the user.

A laser can be provided for the production of an electromagnetic field.

Alternatively, a microwave generator can be provided for the production of an electromagnetic wave when there is a high dust or particle density. Reflection is poorer of a microwave because of its greater wavelength, so that at higher particle concentrations, the saturation of the signal is reached substantially later. Thus it is preferred in coal power stations, in which large amounts of coal are milled, to use microwaves for mass flow determination.

Additional embodiments of the invention are set out in the further dependent claims.

BRIEF DESCRIPTION OF THE DRAWINGS

The invention with its essential details is explained in detail hereinafter using the drawings.

In the drawings:

FIGS. 11–16 are schematic representations for comparison of the mass flow signals at different conveying speeds, FIGS. 17–22 are schematic representations for comparison of the mass flow signals at different concentrations of solids.

DETAILED DESCRIPTION OF THE PREFERRED EMBODIMENT

Figure 1:
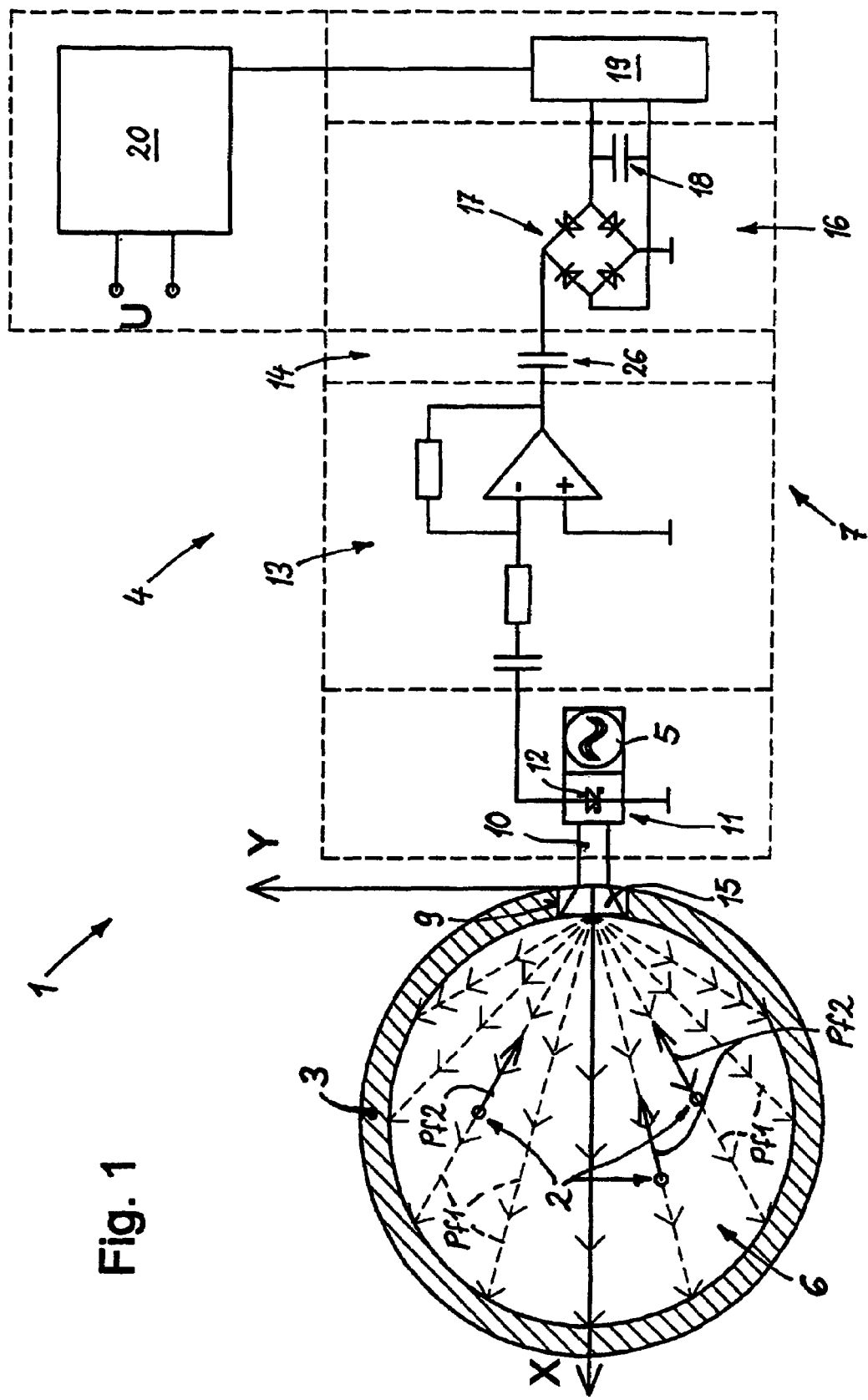
FIG. 1 is a schematic diagram of a mass flow measuring device in connection with a flow channel.

A device 1 shown in FIG. 1 measures the mass flow of a particulate solid 2, which is conveyed using a gas within a flow channel 3. The solid 2 is indicated by a single particle. A measuring device 4 according to the invention is connected laterally to the flow channel 3, and can measure the mass flow or throughput of the solid 2.

The measuring device 4 has a transmitter with an oscillator 5 for producing an electromagnetic field 6 and also a receiver with an evaluation device 7 for measuring the power reflected by the particles of the solid, or the like measure of reflection.

This takes place, as described in more detail herein below, in that the mass flow is formed from the amount of reflection alone. For this purpose, the reflection is measured at least on the solid within the measurement region of the electromagnetic field, from the time course of the measurement signal of the differential quotient of according to time, and the absolute value formed therefrom.

The measure of reflection can, as previously mentioned, be proportional to a function of the reflected power, or else proportional to a function of the reflected energy or a function of the reflected intensity or a function of the reflected radiation flow.

A measurement region covering the cross section of the flow channel is defined within the electromagnetic field, in which the electromagnetic radiation reflected from the solid is evaluated.

This takes place, as described in more detail hereinbelow, in that the mass flow is determined from the amount of reflection alone. For this purpose, the reflection is measured at least from the solid within the measurement region of the electromagnetic flow, from the time course of the measurement signal of the differential quotient according to time, and the absolute value formed therefrom.

In the device 1 shown in FIG. 1, a microwave field is produced as the electromagnetic field by a Gunn oscillator 5 with a Gunn diode. The microwave field produced is conducted from the Gunn diode via a hollow conductor 10 to a horn antenna 15, and from this is irradiated through a wall aperture 9 of the flow channel 3 into the flow channel 3.

The electromagnetic field irradiated into the flow channel 3 is indicated by dashed arrows.

The hollow conductor as intermediate element is in particular advantageous when the flow channel and/or the solid is particularly hot.

The waves reflected from the solid 2 and indicated by the arrows Pf 2 reach a detector 11, which is formed by a Schottky diode as a reflection receiver in the exemplary embodiment according to FIG. 1.

The sensor formed of transmitter and receiver is constructed here as a transceiver, i.e. the sensor transmits and receives simultaneously. The Gunn diode and the Schottky diode are built together into a housing. These microwave modules are obtainable as standard parts (e.g., Macon 86849-M01).

The Schottky diode 12 converts the microwaves into an electrical voltage signal. This voltage from the Schottky diode 12 is not proportional to power over the whole measurement region. However, this is insignificant for the generation of the mass flow signals, since arbitrary functions of the power are suitable for this. The voltage at the Schottky diode results both from the irradiated power and also from the received power; therefore, in this embodiment, the mass flow signal is not determined using the common power, but from the ratio of irradiated power to received power. The function block connected to the Schottky diode 12 includes a differentiator 13, through which the differentiation of the Schottky diode supplied signal takes place. Through this a differential quotient over time if formed. There is adjoined an intermediate stage 14 with a capacitor 26 by which a null point displacement is effected, by means of which and whereby a separation of this constant direct current portion takes place.

The signal is then supplied to a rectifier stage 16 with a bridge rectifier and is rectified there. Mathematically, a sum formation is effected with the measurement signal derived with the differentiator 13. The rectified signal is smoothed with a capacitor 18. This signal represents the mass flow signal, and is the integral formed over time of the amount of the reflected power according to time.

This signal can now be supplied to a digital unit, consisting of an A/D converter 19 and processor 20. The processor can convert the signal to a magnitude which is reasonable for the user.

The possibility also exists of placing the digital unit directly behind the circuit which differentiates the signal. In this case, the processor must continue the null point displacement and the rectification of the signal, which is possible in principle but requires processors with high computing power. It is likewise possible to set the processor directly on the Schottky diodes; A/D converters are then of course then required with a substantially higher precision, and processors with still more computing power.

Figure 2:
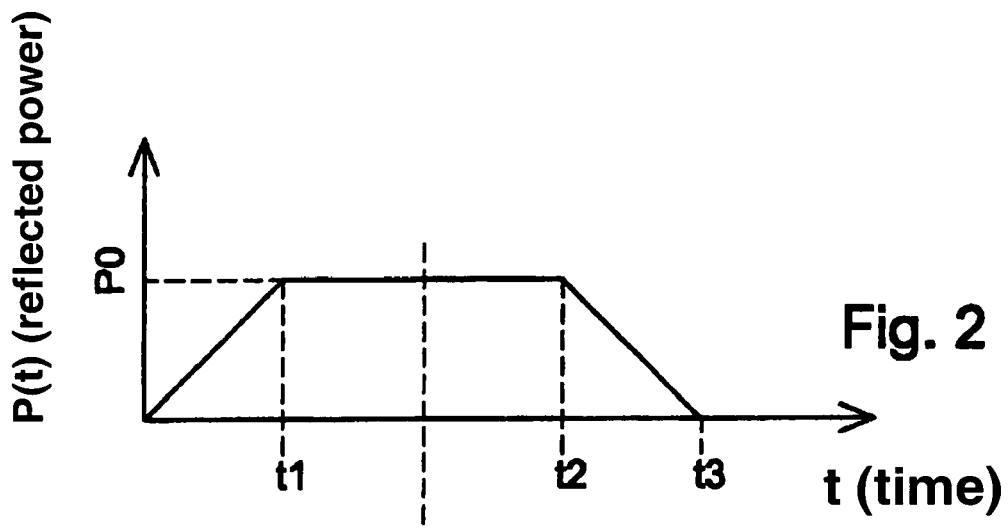
FIGS. 2–3 are two diagrams showing the power reflected by a particle being applied over time.
Figure 3:
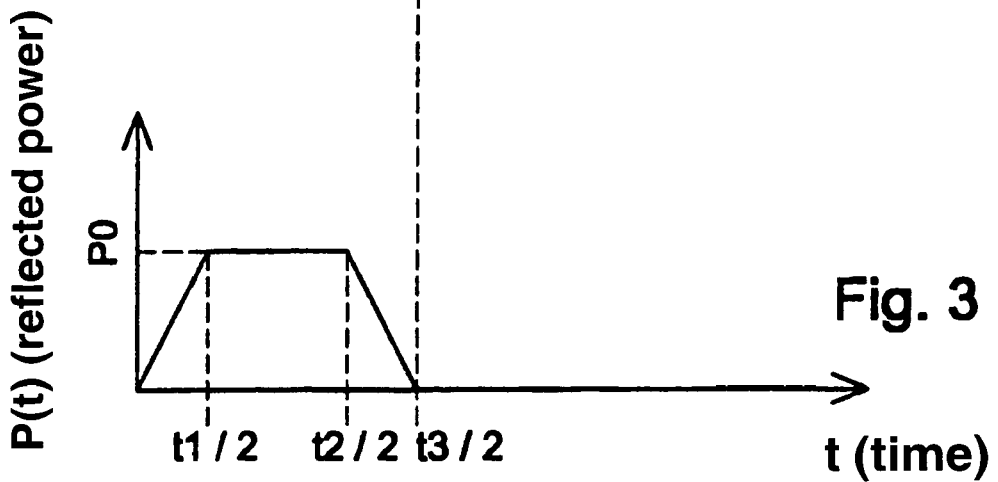

In FIGS. 2–16, the physical connections of the invention are shown. FIGS. 2 and 3 show the power reflected from a solid particle over time at different conveying speeds. It is assumed for simplicity that the electromagnetic field just rises linearly up to a first position at P0, then runs constant to a second position, to then fall linearly again to zero.

Corresponding to this assumed course of the field, the reflected power of a particle at a conveying speed V1 is as shown in FIG. 2. If now the conveying speed is doubled to $V_2 = 2*V_1$, the course of the curve shown in FIG. 3 results.

The areas under the curves in FIGS. 1 and 2 correspond to the energy which a particle reflects on passing through the field. It can be seen that at a doubled speed only half as much energy is reflected as at a single speed. However, since at double the speed and the same particle concentration, the overall reflected energy of all particles which are located exactly in the field is exactly as large as when the particles with single speed are transported (cf. U.S. Pat. No. 5,550,537). Lastly, the total reflected energy is thus a measure of the concentration and not of the mass flow.

Figure 4:
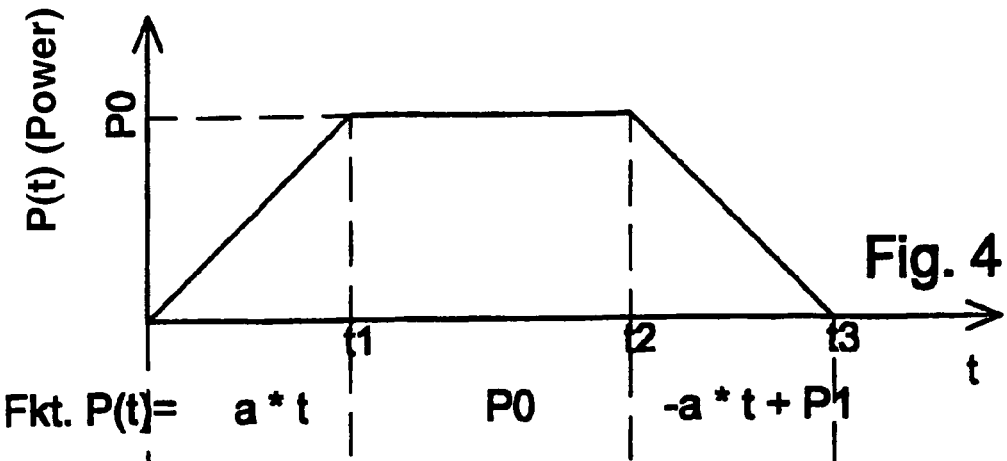
FIG. 4 is a diagram generally corresponding to FIG. 2, with the reflected power of a particle over time.
Figure 5:
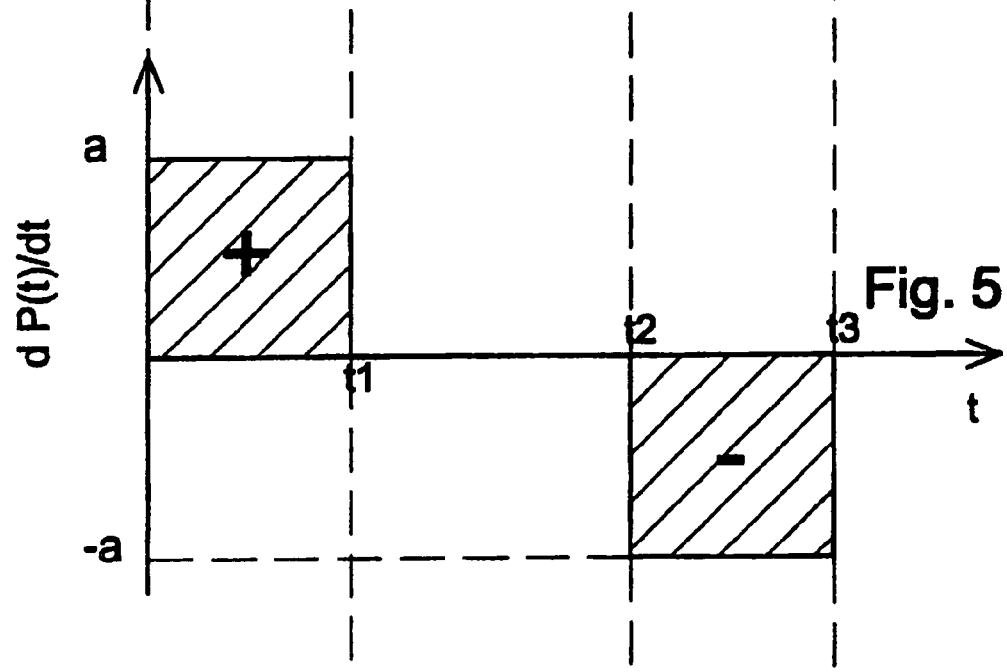
FIG. 5 is a diagram that represents the reflected power after forming the differential quotient according to time.
Figure 6:
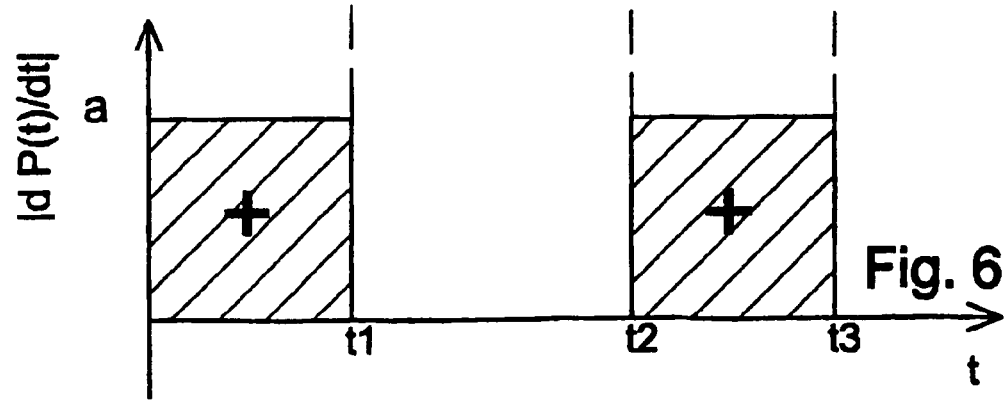
FIG. 6 is a diagram with a representation of the sums of the derivative of the reflected power.
Figure 7:
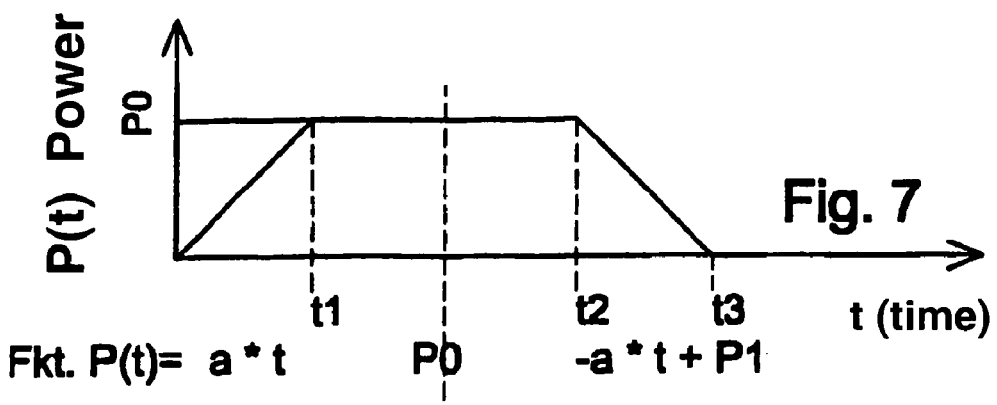
FIGS. 7–10 are diagrams generally corresponding to FIGS. 4 and 6, at different conveying speeds.
Figure 8:
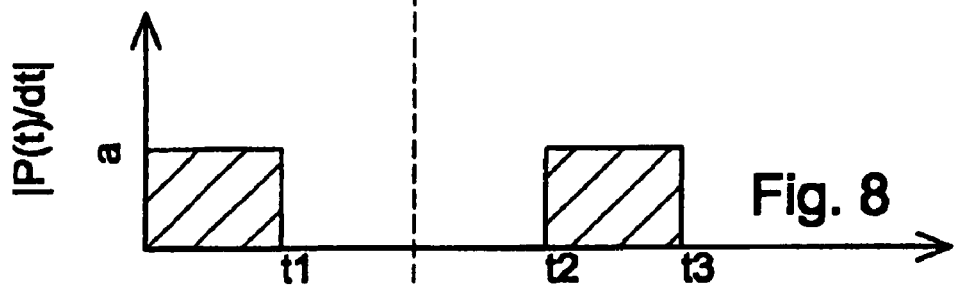
Figure 9:
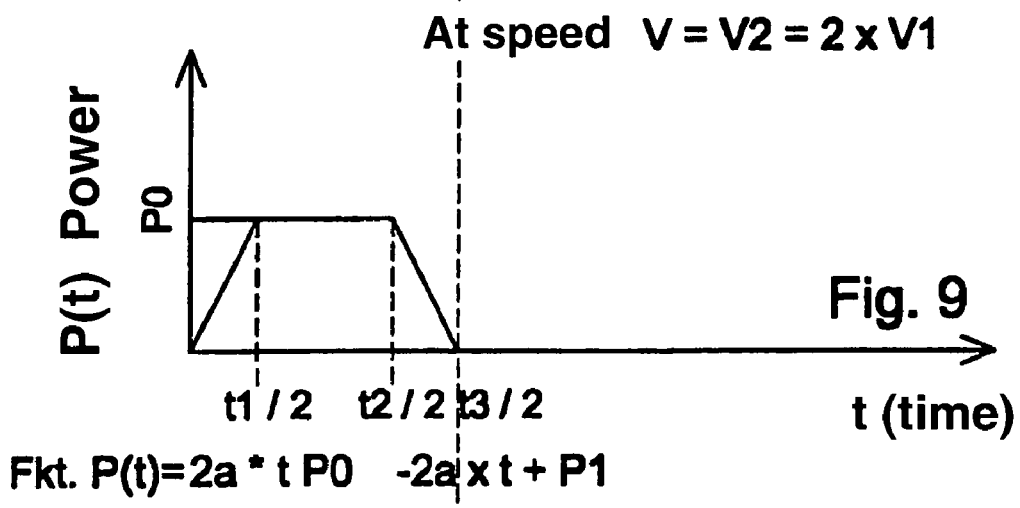
Figure 10:
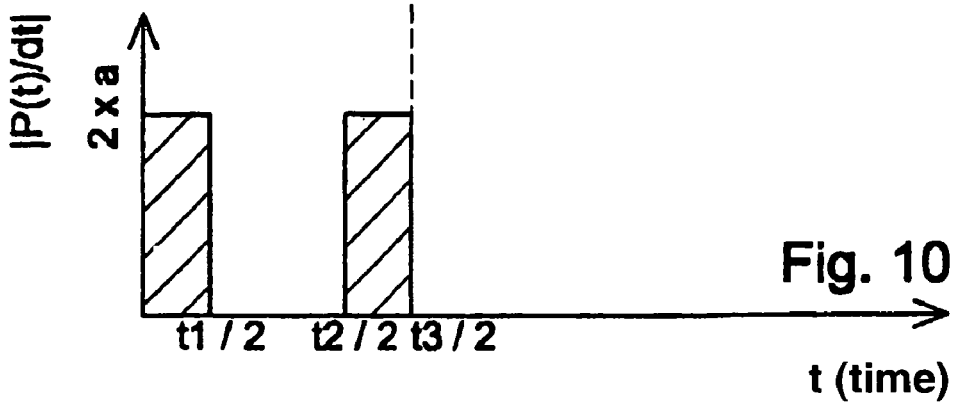

FIGS. 4–6 show how the mass flow can be determined from the measurement of the reflected power or the like reflection measurement.

FIG. 4 shows the reflected power P(t) of a solid particle with a field geometry such as was used as the basis in FIGS. 2 and 3.

If the field strength of the field increases linearly, the reflected power P(t) can be described by a*t with the simplification that the amount of the reflected power is constant, independently of the angle which the direction of light of the particle forms to the sensor. Furthermore it is assumed that the velocity of the particle is constant.

If the reflected power is constant, P0, then, $$P(t) = P0 \qquad \text{Equation 3:}$$

If the reflected power is linear, then:

$$P(t) = -a*t + P1 \qquad \text{Equation 4:}$$

Taking the derivatives of these equations with respect to time, for the linearly rising portion:

$$dP(t)/dt = a \qquad \text{Equation 5:}$$

for the Constant portion:

$$dP(t)/dt = 0 \qquad \text{Equation 6:}$$

and for the portion falling linearly:

$$dP(t)/dt = -a \qquad \text{Equation 7:}$$

Mathematically, as can be seen from FIG. 5, the area under the curve for the linearly falling portion is negative and for the linearly rising portion is positive. This is expressed in FIG. 5 by a plus sign and minus sign in the hatched surfaces. However, the actual area under the curves is to be determined (FIG. 6). For this reason the absolute value is formed. The thus hatched surface is the integral formed over time of the absolute value of reflected power, derived over the time.

The integral over the amount of the time derivative of the reflected power is thus proportional to the mass flow. Furthermore, the integral formed over time of the reflected power derived according to time is termed the mass flow signal.

Equation 8:

$$\text{mass flow signal} = \int \left| \frac{(\partial P(t))}{(\partial t)} \right| dt$$

Here: P=reflected power
t=time

The thus formed measurement result is proportional to the mass flow, since each particle produces an equally large mass flow signal, independent of speed. This is indicated in FIGS. 7–10, the speed being $V=V_1$, while in FIGS. 9 and 10 the speed $V=V_2=2*V_1$.

The mass flow signal is equal at both speeds, since the area under the curve is equal at both speeds.

For speed $V=V_1$, the area is calculated as follows:

$$\text{mass flow signal } V_1 = a*t1 + a*(t3-t2) \qquad \text{Equation 9:}$$

with (t3−t2)=t1 gives $$\text{mass flow signal } V_1 = 2a*t1 \qquad \text{Equation 10:}$$

for a speed $V=V_2=2*V_1$, the area is calculated as follows:

$$\text{mass flow signal } V_2 = 2a*(t1)/2 + 2a*(t3-t2)/2 \qquad \text{Equation 11:}$$

with (t3−t2)=t1, there holds (cf. FIG. 10):

$$\text{mass flow signal } V_2 = 2a*t1 \qquad \text{Equation 12:}$$

Thus on passing across the field, each particle produces, independently of its speed, an identical signal, provided that each particle has the same geometry and that their other material properties are identical. A comparison of FIGS. 2 and 3 shows that only the reflected energy is considered there. In this case, a particle moving twice as fast produces only half as large a signal as a particle traversing the field half as fast.

The consequence is clear in FIGS. 11–16. In FIGS. 14–16, a conveying state is shown in which the solid particles are passed through with twice the speed of those in the conveying state shown in FIGS. 11–13.

The mass flow signal for the respective conveying state already mentioned is shown in FIGS. 12 and 15.

It can be seen in FIGS. 13 and 16 that in the conveying state shown on the right-hand side in which the mass flow is twice as large for that shown on the left-hand side, a mass flow signal twice as large can also be measured. The individual hatched surfaces present, as shown on the left-hand side in the time window are all of equal size, but on the right-hand conveying state there are twice as many hatched rectangles as for the conveying state on the left-hand side.

In order to indicate that the mass flow signal produced according to the measures of this patent, it is shown in FIGS. 17–22 that for two conveying states with the same speed but different concentration, the mass flow signal is likewise correlated with the mass flow and not with the speed.

It can be seen in these Figures that with the conveying state shown on the left-hand side, the concentration is only half as great as for the conveying state shown on the right-hand side. Since both conveying states have the same speed, the mass flow signal of a particle is also identical for the two conveying states (FIGS. 18 and 21). The conveying state shown on the left-hand side conveys with only half the throughput as that shown on the right-hand side; the mass flow signal behaves correspondingly. In the time window on the left-hand side corresponding to FIG. 19, only half as many hatched surfaces are present as on the right-hand side according to FIG. 22.

Expressed illustratively, in this measurement method the particles are counted, because each particle produced the same signal independently of the concentration and the speed at which it is conveyed. Larger particles produce larger signals than smaller particles of the same kind. If a larger particle reflects k times more power that smaller, then:

Equation 13:

$$\int \left| \frac{(\partial P2(t))}{(\partial t)} \right| dt = \int \left| \frac{\partial (k*P1(t))}{(\partial t)} \right| = k \int \left| \frac{(\partial P1(t))}{(\partial t)} \right| dt$$

Thus also the mass flow signal is k times greater, when a larger particle reflects k times more power. Thus not only can particles be counted but also the weight of an individual particle can be correctly determined.

Thus it can finally be said that the integral over the sum of the reflected power derived according to time is very well correlated with the mass low. It is a general rule the correlation is linear, but this does not always have to be so.

It is theoretically sufficient to measure only the total reflected power, since with signal generation in an intermediate stop the derivative of the reflected power is formed, with which constant fractions of reflected power likewise fall out of the calculation, so that reflected power from pipe wall and/or adherent deposits do not lead to a false result. Since the fraction of reflected power from pipe walls and/or adherent is often very much greater than that reflected from the solid, this however leads to a poor signal/noise ratio. It is therefore more favorable to measure only the power of the electromagnetic wave reflected at the solid. The Doppler effect can be used for this purpose, in that only the power of frequency-shifted electromagnetic waves is used to produce the mass flow signal. Furthermore it is possible to use the difference from the entitled and reflected power instead of the reflected power to generate the mass flow signal. Particularly when the irradiated power is constant or undergoes a known time variation.

The equivalence of the measurement of the ratio of reflected to irradiated power is a pure power measurement, may be explained briefly by the example of a constant irradiated power.

Equation 14:

$$\int \left| \frac{\left(\frac{\partial (Pr(t))}{Pa}\right)}{(\partial t)} \right| dt = \frac{1}{Pa} \int \left| \frac{(\partial Pr(t))}{(\partial t)} \right| dt$$

with $P_a$=irradiated power=constant
$P_r(t)$=reflected power.

Since the constantly irradiated power or respectively the inverse ratio thereof, may mathematically be taken out before the integral, calibration into weight units per time unit must be solely by means of this constant factor, so that likewise the mass throughput can be determined. In the example shown here, the extent of the field has been taken as greater than the particle size; however, the measurement effect is independent of the ratio of field extent to particle size.

Furthermore, the measurement effect was shown at only a few special fields and the further limitation is made that this reflected power is independent of the angle which the direction of flight makes to the sensor. However this is only a simplification of the representation. The measuring effect works also without this limitation and at given fields. It is decisive that the reflected power depends only on the particle geometry, the specific properties of the material, and the irradiated power of the sensor.

Thus for the reflected power of two particles one of which moves twice as fast as the other, with a given field and taking into account the angle which the direction of flight of the particle makes with the sensor:

$$V_1 = 2*V_2 \quad \text{Equation 15:}$$

so that $$P_1(t) = P_2(2t) \quad \text{Equation 16:}$$

A voltage or a current is usually produced in an electrical measuring device, and is proportional to the quantity to be measured. However, there are cases where this is not possible, and the voltage or the current produced is only proportional to a function of the quantity to be measured. In this case, Equation 16 must be extended to:

$$f(P_1(t)) = f(P_2(t)) \quad \text{Equation 17:}$$

$P_1$=reflected power from particle 1
$P_2$=reflected power from particle 2
t=time
$V_1$=speed of particle 1
$V_2$=speed of particle 2
f=symbol for function It is to be noted that a particle which passes twice as fast through the field of a sensor than a second similar particle which produces the same signal. Expressed formally in Equation 18.

Equation 18:

$$\int_0^{T_o} \left| \frac{\partial P1(t)}{\partial t} \right| dt = \int_0^{2*T_o} \left| \frac{\partial P2(t)}{\partial t} \right| dt$$

This should be substantially more valid general case of

Equation 19:

$$\int_0^T \left| \frac{\partial f(P1(t))}{\partial t} \right| dt = \sum_0^{2*T} \left| \frac{\partial f(P2(t))}{\partial t} \right| dt$$

This case is generally valid, because the constant $T_0$ is replaced with the variable T. $T_0$ is a special case of t. Furthermore all functions of the power are taken into account.

For evaluation, Equation 17 is inserted into the left-hand position of Equation 19:

Equation 20:
$$\int_0^T \left|\frac{\partial f(P1(t))}{\partial t}\right| dt = \int_0^T \left|\frac{\partial f(P2(2t))}{\partial t}\right| dt$$

only u is substituted for 2t, resulting in $$u = 2t \quad \text{Equation 21:}$$

this is equivalent to

Equation 22:
$$\frac{u}{2} = t$$

In equation 22, t is now differentiated in respect to time:

Equation 23:
$$\frac{du}{dt} = 2$$

This is equivalent to

Equation 24:
$$\frac{du}{2} = dt$$

Hereinbelow, Equation 22 and Equation 24 are substituted in Equation 20. Furthermore, first the outer and then the inner derivative are formed within the summation signal:

Equation 25:
$$\int_0^T \left|\frac{\partial f(P2(2t))}{\partial t}\right| dt = \int_0^{2*t} \left|\frac{\partial f(P2(u))}{\partial u} \frac{\partial u}{\partial t}\right| \frac{du}{2}$$

with Equation 23 gives:

Equation 26:
$$\frac{\partial u}{\partial t} = 2$$

Equation 26 is now inserted into Equation 25, resulting in

Equation 27:
$$\int_0^{2*t} \left|\frac{\partial f(P2(u))}{\partial u} \frac{\partial u}{\partial t}\right| \frac{du}{2} = \int_0^{2*t} \left|\frac{\partial f(P2(u))}{\partial u} 2\right| \frac{du}{2}$$

Constants also have to be taken out of the sum and should therefore be abbreviated; thus there results from Equation 28

Equation 28:
$$\int_0^{2*t} \left|\frac{\partial f(P2(u))}{\partial u} 2\right| \frac{du}{2} = \int_0^{2*t} \left|\frac{\partial f(P2(u))}{\partial u}\right| du$$

Since the result of an integral does not depend on the sign of the variables and constraints, Equation 28 can be written as:

Equation 29:
$$\int_0^{2*t} \left|\frac{\partial f(P2(u))}{\partial u}\right| du = \int_0^{2*t} \left|\frac{\partial f(P2(t))}{\partial t}\right| dt$$

The assertion is thus proved. The constant 2 can be replaced by another given constant without further proof, so that in the most general case as Equation 32:

When Equation 30: $V_1 = a * V_2$ holds, then likewise Equation 31: $P_1(t) = P_2(a*t)$ holds, so that To/a Equation 32:
$$\int_0^{a*To} \left|\frac{\partial f(P2(t))}{\partial t}\right| dt = \int_0^{To/a} \left|\frac{\partial f(P2(t))}{\partial t}\right| dt$$

This means the signal magnitude G as in Equation 33:

$$G = \int \left|\frac{\partial f(P(t))}{\partial t}\right| dt$$

is independent of the speed. Each particle of the same kind which passes through the field of a sensor which generates this measurement quantity produces the same signal G independent of its speed. Now only the sum of all these signals has to be formed and measured over a given time; then a signal is obtained which is proportional to the number of particles which were transported through the field in this given time. Since not only are particles counted, but simultaneously also larger particles produce more signal, the weight of the particles is also detected, so that finally the signal is proportional to the mass flow.

As already mentioned, this kind also functions to determine the mass flow if not only the power can be directly determined, hereby a function of the power, for example $P^2$.

This can be seen if for $P_1$ and $P_2$ respectively $P_1^2$ and $P_2^2$ are respectively inserted in Equation 33:

Equation 34:
$$G_1 = \int_o^{To} \left|\frac{\partial (P_1^2(t))}{\partial t}\right| dt$$

Equation 35:

If the outer derivative is formed respectively within the sum, these results:

Equation 36:

Equation 37:

With the respective Equation 18 or 19, there directly follows that G1=G2, since

Equation 36/37:
$$G_1 = 2\int_o^{To}\left|\frac{\partial(P1(t))}{\partial t}\right|dt = G_2 = 2\int_o^{2*To}\left|\frac{\partial(P2(t))}{\partial t}\right|dt$$

This has a direct consequence if microwaves are used as the electromagnetic waves. For measuring the power of the reflected microwaves, relatively inexpensive diodes can be used. These however have the disadvantage that the output voltage is not proportional to the power. The Schottky diode shows a kind of saturation behavior at high powers, since the characteristic of the Schottky diode flattens out. Since however it is not the power which has to be determined with the signal magnitude, but the mass flows signal using only the characteristic, or the output voltage of the Schottky diode as a function of the power, this means that there is no disadvantage, and the inexpensive Schottky diodes can be used without the characteristic having to be linearized.

Figure 23:
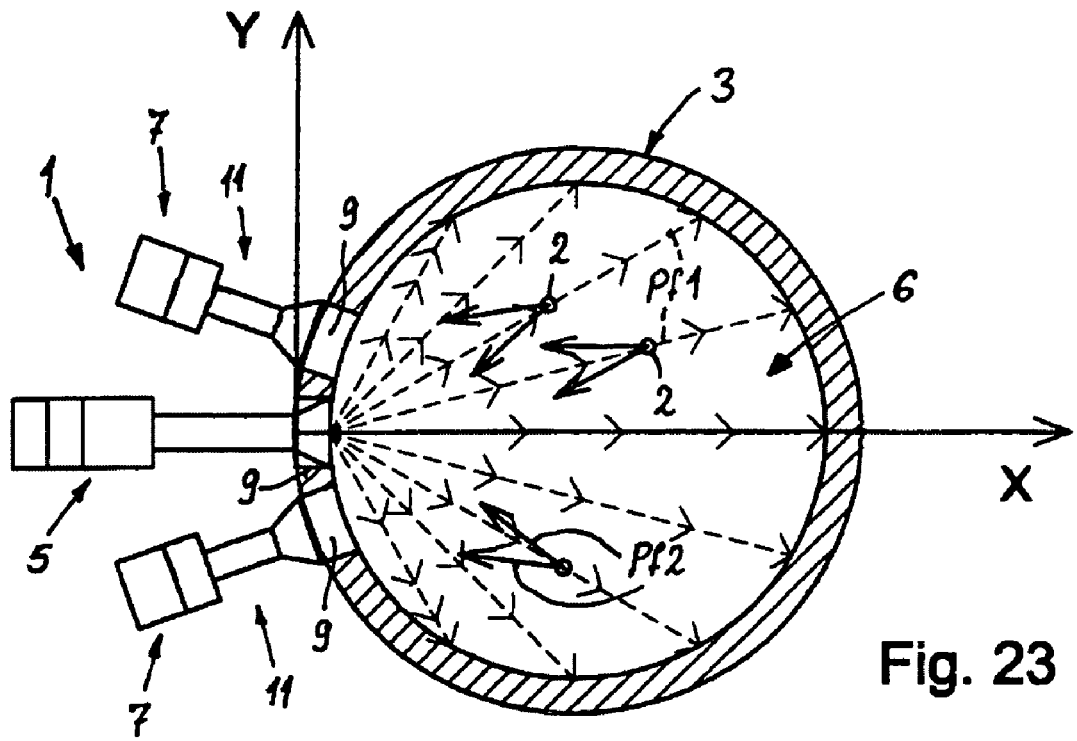
FIG. 23 is a schematic diagram of a mass flow measurement device with microwaves coupled-in and coupled-out at different places of a flow channel.
Figure 24:
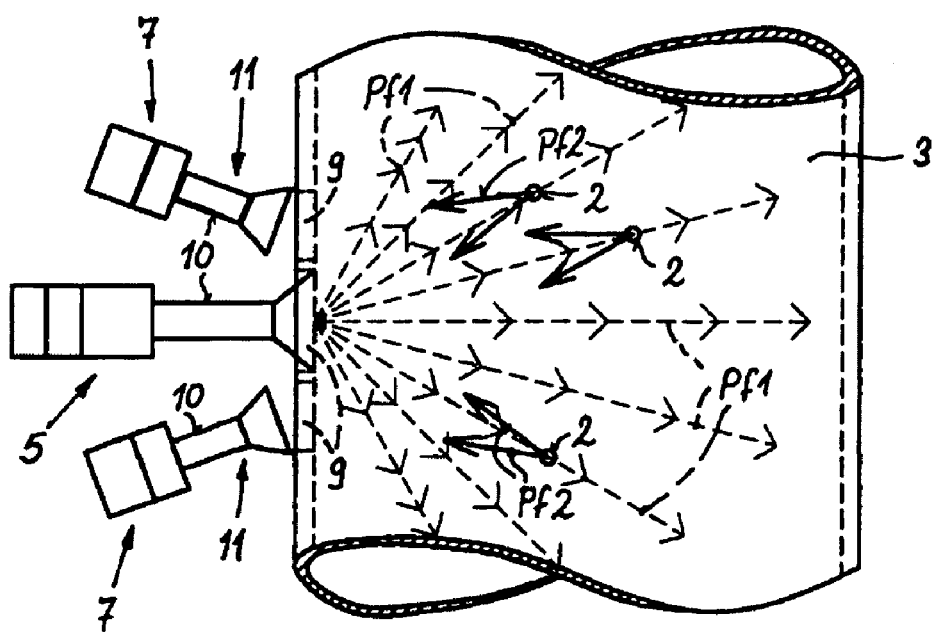
FIG. 24 is a side view of the arrangement shown in FIG. 17.

FIGS. 23 and 24 show a measurement arrangement which is generally comparable to FIG. 1. The receiver transmitter however do not form a unit here, but are arranged separately. There are several receivers; it is to be indicated that the receivers can be installed above and below, and also right and left, of the transmitter.

Exhaust air mostly contains only slight amounts of dust. It is often necessary to measure the amount of dust in order to maintain legal standards. This can take place using the devices according to the invention, corresponding for example to FIG. 1 or FIGS. 23 and 24.

Figure 25:
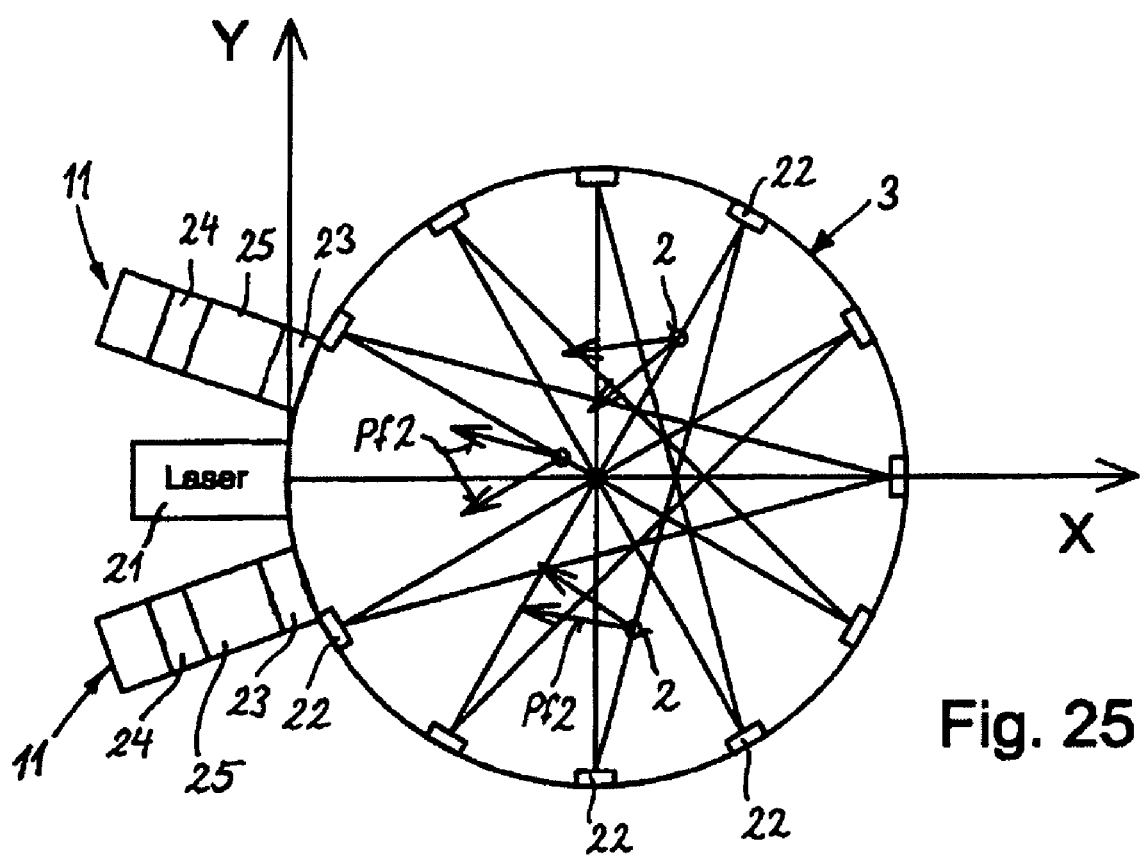
FIG. 25 is a diagram, generally corresponding to FIG. 17, of a mass flow measuring device in connection with a flow channel, using a laser for producing an electromagnetic field.

For example, in FIG. 25 a laser 21 is installed on a chimney or exhaust air channel as the flow channel 3. Plural reflectors are installed on the inner wall of the chimney or exhaust air channel, and reflect the laser back and forth so that the greatest possible region of the cross section is detected. The detector(s) which measure the reflective power can be installed laterally of, or above or below, the laser 21. The receiver can have a condenser 23 which focuses the reflected light onto a photocell 24. If the reflection is too weak, a photomultiplier 25 can be placed between the condenser 25 and the photocell 24. The photocell generates, from the reflected power of the electromagnetic wave, a voltage or a current signal, which has to be differentiated in the next step. For this, and for the further steps, the measuring device according to FIG. 1 can be used.

The photocell 24 or a phototransistor can be used, instead of the Schottky diode 12 used as detector 12 there.

Alternatively according to the arrangement, according to FIG. 25, the cross section of the flow channel 3 can be scanned using a laser, the laser being continuously or discontinuously sweeping over the cross section, so that this is detected as completely as possible.

With a higher dust or particle density, it is advantageous to use a microwave as the electromagnetic wave. They are poorly reflected because of their greater wavelength, so that at high particle concentrations, the saturation of the signal is reached substantially later. For example, in coal power stations, in which large amounts of coal are comminuted, microwaves can therefore advantageously be used for mass flow determination.

The invention claimed is:

1. Method of measuring a mass flow of a particulate solid which is transported by a gas through a defined measurement region, and an electromagnetic radiation reflected from the solid being evaluated, comprising determining the mass flow only from a measure of reflection by measuring the reflection at least from the particulate solid (2) within the measurement region of the electromagnetic field (6), wherein an area under a curve of a time course of a measurement signal collectively represents reflected energy and a measure of a concentration of the particulate solid, and determining a differential quotient according to time, or a derivative of higher order, from a time course of a measurement signal, and an absolute value is formed therefrom to determine a particle count signal independent of particle speed whose area is a measure for a particle magnitude, and determining a mass flow signal by integrating over time of an amount of the reflected radiation, derived over time.

2. Method according to claim 1, wherein the signal available after absolute value formation is integrated for signal damping.

3. Method according to claim 1, wherein the measure of reflection is proportional to a function of reflected power or a function of reflected energy or a function of a reflected intensity or a function of a reflected radiation flux.

4. Method according to claim 1, wherein a total reflected power is measured.

5. Method according to claim 1, wherein only radiation reflected from the solid (2) is measured using the Doppler effect to measure a frequency shifted reflected radiation.

6. Method according to claim 1, wherein with power radiated at a constant or known level or subject to a known variation with time, the mass flow signal is generated from z difference of radiated and reflected radiation or from a ratio of radiated and reflected radiation.

7. Method according claim 1, wherein laser light or microwaves are used as the electromagnetic radiation.

8. Device for measuring the mass flow of a solid (2) transported using a gas, comprising an arrangement (5) for producing an electromagnetic field (6) in which a measurement region is defined, an evaluation device (7) connected to a detector (11) for radiation reflected at least from a solid (2), wherein the evaluation device has a differentiator (13) connected to the detector (11) for detecting reflected electromagnetic radiation, and a rectifier (17) connected for absolute value formation to the differentiator (13) for determining a count impulse independent of particle speed, whose area is a measure for particle size, and an integrator for determining a mass flow signal by integration over time of an amount of the reflected radiation, derived over time.

9. Device according to claim 8 wherein an intermediate stage (14) for null point displacement is inserted between the differentiator (13) and the rectifier (17), and includes a capacitor (26) for DC voltage separation.

10. Device according to claim 8, wherein a capacitor (18) is provided for smoothing the output signal of the rectifier (17).

11. Device according to claim 8, wherein a portion of a signal preparation is provided by an analog circuit and another portion of the signal preparation is provided by a digital circuit, and wherein the analog circuit is provided for differentiation for determination of a differential quotient, and a digital circuit is provided for absolute value formation and integration.

12. Device according to claim 8, wherein an output of the rectifier (17), with the output signal arising there, if necessary after smoothing by a capacitor (18), is connected to a digital function unit with an A/D converter (19) and a processor (20).

13. Device according to claim 8, wherein a digital circuit is provided for signal generation, and for this purpose the detector (11), if necessary after impedance matching, is directly connected to an A/D converter which is connected to a processor.

14. Device according to claim 8, wherein the mass flow measurement device (4) is connected to a flow guide (3), such as a chimney, an exhaust channel, or a like channel; and wherein for this purpose a lateral opening is provided in a wall of the channel through which the generated magnetic field (6) can be radiated into the channel transversely of a mass flow conveying direction in the channel, and a reflected beam power or the like can be coupled out.

15. Device according to claim 8, wherein the device (5) for producing an electromagnetic field (6) has a microwave generator.

16. Device according to claim 15, wherein the microwave generator has a Gunn diode; wherein the detector (11) has a Schottky diode (12) as receiving element and wherein the Gunn diode and the Schottky diode are included in a microwave module as a transceiver.

17. Device according to claim 16, wherein a hollow conductor (10), if necessary with a horn antenna arranged at one end, is provided between the microwave module and the measurement region.

18. Device according to claim 8, wherein the device for producing an electromagnetic field (6) includes a laser (21).

19. Device according to claim 18, wherein a deflecting device is provided for scanning a laser beam within the measurement region.

20. Device according to claim 18, wherein one or more reflectors (22) for the laser beam are installed within the measurement region.

21. Device according to claim 18, wherein the detector (11) has a photocell (24) or a photoresistor, preferably with collecting optics (23) arranged before it, if necessary with a photomultiplier (25) arranged therebetween.

* * * * *